United States Patent
Bruder et al.

(12) 
(10) Patent No.: US 10,105,259 B2
(45) Date of Patent: Oct. 23, 2018

(54) WOUND AND THERAPY COMPRESS AND DRESSING

(71) Applicant: BRUDER HEALTHCARE COMPANY, Alpharetta, GA (US)

(72) Inventors: Mark H. Bruder, Alpharetta, GA (US); Aaron N. Ingram, Canton, GA (US)

(73) Assignee: BRUDER HEALTHCARE COMPANY, LLC, Alpharetta, GA (US)

( * ) Notice: Subject to any disclaimer, the term of this patent is extended or adjusted under 35 U.S.C. 154(b) by 575 days.

(21) Appl. No.: 14/331,874

(22) Filed: Jul. 15, 2014

(65) Prior Publication Data

US 2014/0330222 A1 Nov. 6, 2014

Related U.S. Application Data (63) Continuation-in-part of application No. 13/956,727, filed on Aug. 1, 2013, and a continuation-in-part of
(Continued)

(51) Int. Cl.
*A61F 13/00* (2006.01)
*A61F 9/00* (2006.01)
(Continued)

(52) U.S. Cl.
CPC ........... *A61F 9/0026* (2013.01); *A61F 7/02* (2013.01); *A61F 7/08* (2013.01); *A61F 13/00* (2013.01); *A61F 13/00063* (2013.01); *A61F 13/0203* (2013.01); *A61F 13/0226* (2013.01); *A61F 13/124* (2013.01); *A61L 15/18* (2013.01); *A61F 2007/0004* (2013.01); *A61F 2007/023* (2013.01);
(Continued)

(58) Field of Classification Search
USPC ........................................................ 607/109
See application file for complete search history.

(56) References Cited

U.S. PATENT DOCUMENTS 2,066,271 A 12/1936 Irwin
2,882,244 A 4/1959 Milton
(Continued)

FOREIGN PATENT DOCUMENTS

EP 0099748 5/1987
EP 0230387 4/1988
(Continued)

OTHER PUBLICATIONS

Healthcare Packaging; Examining Transdermal Delivery Developments; May 1, 2013; 5 pgs.
(Continued)

*Primary Examiner* — Kim M Lewis
(74) *Attorney, Agent, or Firm* — Gardner Groff Greenwald & Villanueva, PC (57) ABSTRACT

An article for therapy and treatment of at least one eye. The article includes a backing for application to the at least one eye. The backing includes at least one receiver positioned to align with the at least one eye. The article also includes at least one pod that is detachably secured within the at least one receiver. The at least one pod includes material for delivering therapy and treatment to the at least one eye.

20 Claims, 8 Drawing Sheets

Related U.S. Application Data application No. 13/956,717, filed on Aug. 1, 2013, now Pat. No. 9,925,087, and a continuation-in-part of application No. 13/832,626, filed on Mar. 15, 2013, now Pat. No. 9,445,939, which is a continuation-in-part of application No. 13/956,717, which is a continuation-in-part of application No. 13/832,626, application No. 13/291,059, filed on Nov. 7, 2011, now Pat. No. 8,420,882, which is a continuation of application No. 10/380,803, filed on May 30, 2003, now Pat. No. 8,524,973, application No. 13/956,727, which is a continuation-in-part of application No. 10/380,803, filed as application No. PCT/US01/28908 on Sep. 17, 2001, now Pat. No. 8,524,001.

(60) Provisional application No. 60/232,826, filed on Sep. 15, 2000.

(51) Int. Cl.
*A61F 7/02* (2006.01)
*A61F 13/02* (2006.01)
*A61L 15/18* (2006.01)
*A61F 13/12* (2006.01)
*A61F 7/08* (2006.01)
*A61F 7/00* (2006.01)

(52) U.S. Cl.
CPC . *A61F 2007/0204* (2013.01); *A61F 2007/026* (2013.01); *A61F 2007/0225* (2013.01); *A61F 2007/0228* (2013.01); *A61F 2007/0242* (2013.01); *A61F 2007/0261* (2013.01); *A61F 2007/0263* (2013.01); *A61F 2013/0017* (2013.01); *A61F 2013/0091* (2013.01); *A61F 2013/00165* (2013.01); *A61F 2013/00187* (2013.01); *A61F 2013/00246* (2013.01); *A61F 2013/00544* (2013.01); *A61F 2013/00582* (2013.01); *A61F 2013/00727* (2013.01); *A61F 2013/00736* (2013.01); *A61F 2013/00855* (2013.01); *A61F 2013/00936* (2013.01)

(56) References Cited

U.S. PATENT DOCUMENTS

| | | |
|---|---|---|
| 3,008,803 A | 11/1961 | Milton |
| 3,010,789 A | 11/1961 | Milton |
| 3,012,853 A | 12/1961 | Milton |
| 3,013,982 A * | 12/1961 | Breck .................. B01J 20/186 208/2 |
| 3,030,181 A | 4/1962 | Milton |
| 3,587,578 A * | 6/1971 | Walker .................. A61F 7/02 604/304 |
| 4,000,028 A | 12/1976 | Hoey |
| 4,108,478 A | 8/1978 | Higashijima |
| 4,273,621 A | 6/1981 | Fornoff |
| 4,516,564 A | 5/1985 | Koiso et al. |
| 4,525,410 A | 6/1985 | Hagiwara et al. |
| 4,775,585 A | 10/1988 | Hagiwara et al. |
| 4,826,497 A | 5/1989 | Marcus et al. |
| 4,882,349 A | 11/1989 | Baglioni |
| 4,897,297 A | 1/1990 | Zafiroglu |
| 4,906,466 A | 3/1990 | Edwards et al. |
| 4,919,648 A | 4/1990 | Sibalis |
| 4,988,053 A | 1/1991 | Choi |
| 5,019,254 A | 5/1991 | Abrevaya et al. |
| 5,028,435 A | 7/1991 | Katz et al. |
| 5,123,900 A | 6/1992 | Wick |
| 5,135,518 A | 8/1992 | Vera |
| 5,179,944 A | 1/1993 | McSymytz |
| 5,314,005 A | 5/1994 | Dobry |
| RE34,692 E | 8/1994 | Becher |
| 5,366,491 A | 11/1994 | Ingram |
| 5,409,472 A | 4/1995 | Rawlings et al. |
| 5,413,788 A | 5/1995 | Edwards et al. |
| 5,447,531 A | 9/1995 | Wood |
| 5,697,961 A | 12/1997 | Kiamil |
| H1732 H | 6/1998 | Johnson |
| 5,846,559 A | 12/1998 | Hopp |
| 5,890,487 A | 4/1999 | Kimmel |
| 5,900,258 A | 5/1999 | Engler |
| 5,935,486 A | 8/1999 | Bell et al. |
| 5,977,428 A | 11/1999 | Bozigian et al. |
| 5,984,995 A | 11/1999 | White |
| 6,017,606 A | 1/2000 | Sage et al. |
| 6,019,782 A | 2/2000 | Davis et al. |
| 6,045,820 A | 4/2000 | Messier |
| 6,169,223 B1 | 1/2001 | Mahr et al. |
| 6,353,145 B1 | 3/2002 | Church |
| 6,409,746 B1 | 6/2002 | Igaki et al. |
| 6,576,004 B2 | 6/2003 | Johnston |
| 6,592,888 B1 | 7/2003 | Jensen et al. |
| 6,617,490 B1 | 9/2003 | Chen et al. |
| 6,641,264 B1 | 11/2003 | Schwebel |
| 6,752,998 B2 | 6/2004 | Verdrel-Lahaxe et al. |
| 6,823,860 B2 | 11/2004 | Igaki |
| 6,874,884 B2 | 4/2005 | Schwebel |
| 7,036,928 B2 | 5/2006 | Schwebel |
| 7,221,070 B2 | 5/2007 | Soroudi |
| 7,231,922 B2 | 6/2007 | Davison et al. |
| 7,357,500 B2 | 4/2008 | Schwebel |
| 7,513,893 B2 | 4/2009 | Soroudi |
| 7,559,907 B2 | 7/2009 | Krempel et al. |
| 7,652,228 B2 | 1/2010 | Igaki et al. |
| 7,981,147 B2 | 7/2011 | Korb et al. |
| 8,025,689 B2 | 9/2011 | Korb et al. |
| 8,034,092 B2 | 10/2011 | Bruder et al. |
| 8,109,964 B2 * | 2/2012 | Payne .................. A61F 13/124 606/204.25 |
| 8,114,433 B2 | 2/2012 | Huey et al. |
| 8,202,853 B2 | 6/2012 | Adkins, Jr. |
| 8,235,954 B2 | 8/2012 | Soroudi |
| 8,246,978 B2 | 8/2012 | Kydonieus et al. |
| 8,261,734 B2 | 9/2012 | Dodo |
| 8,319,002 B2 | 11/2012 | Daniels et al. |
| 8,333,793 B2 | 12/2012 | Igaki et al. |
| 8,343,203 B2 | 1/2013 | Ishikawa |
| 8,349,806 B2 | 1/2013 | Brubaker et al. |
| 8,357,189 B2 | 1/2013 | Ugajin et al. |
| 8,420,882 B2 | 4/2013 | Bruder et al. |
| 8,430,921 B2 | 4/2013 | York-Leung |
| 8,506,539 B2 | 8/2013 | Guillon et al. |
| 8,524,973 B2 | 9/2013 | Bruder et al. |
| 8,535,363 B1 | 9/2013 | Lewis |
| 8,617,229 B2 | 12/2013 | Korb et al. |
| 8,642,831 B2 | 2/2014 | Larsen et al. |
| 8,709,039 B2 | 4/2014 | Humphreys |
| 8,747,888 B2 | 6/2014 | Kydonieus et al. |
| 8,636,786 B2 | 7/2014 | Biser |
| 8,778,301 B2 | 7/2014 | Mamelak et al. |
| 8,784,391 B1 | 7/2014 | Biser |
| 8,795,718 B2 | 8/2014 | Bedard et al. |
| 2001/0009831 A1 | 7/2001 | Schink et al. |
| 2002/0032153 A1 | 3/2002 | Whitehouse |
| 2002/0193026 A1 | 12/2002 | Ota et al. |
| 2003/0014096 A1 * | 1/2003 | Burkhart .................. A61F 7/02 607/109 |
| 2003/0060798 A1 * | 3/2003 | Fischer .................. A61N 1/30 604/501 |
| 2003/0208150 A1 | 11/2003 | Bruder et al. |
| 2005/0022823 A1 | 2/2005 | Davison |
| 2005/0187502 A1 | 8/2005 | Krempel |
| 2006/0018953 A1 | 1/2006 | Guillon et al. |
| 2006/0036305 A1 * | 2/2006 | Koby .................. A61F 7/02 607/109 |
| 2007/0009583 A1 | 1/2007 | Qvist |
| 2008/0132978 A1 | 6/2008 | Korb et al. |
| 2008/0200885 A1 | 8/2008 | Schwebel |
| 2008/0251085 A1 | 10/2008 | Schwebel |
| 2009/0137533 A1 | 5/2009 | Adkins, Jr. |
| 2009/0149925 A1 | 6/2009 | MacDonald et al. |
| 2009/0175926 A1 | 7/2009 | Adams |

(56) References Cited

U.S. PATENT DOCUMENTS

| | | | |
|---|---|---|---|
| 2009/0192478 A1 | 7/2009 | Soroudi | |
| 2009/0281507 A1 | 11/2009 | Humphreys | |
| 2009/0287168 A1 | 11/2009 | Mitra et al. | |
| 2009/0287282 A1 | 11/2009 | Biser et al. | |
| 2009/0287283 A1* | 11/2009 | Biser | A61F 7/02 607/109 |
| 2009/0291124 A1 | 11/2009 | Bedard | |
| 2010/0010598 A1 | 1/2010 | Igaki et al. | |
| 2010/0022465 A1 | 1/2010 | Brubaker et al. | |
| 2010/0106109 A1 | 4/2010 | Bruder et al. | |
| 2010/0106111 A1 | 4/2010 | Schwebel | |
| 2010/0145469 A1 | 6/2010 | Barralet et al. | |
| 2010/0256552 A1 | 10/2010 | Korb et al. | |
| 2011/0208279 A1* | 8/2011 | Sanker | A61F 7/02 607/109 |
| 2011/0307041 A1 | 12/2011 | Floyd | |
| 2012/0053537 A1 | 3/2012 | Bruder et al. | |
| 2012/0136285 A1 | 5/2012 | Korb et al. | |
| 2013/0053733 A1 | 2/2013 | Korb et al. | |
| 2013/0071322 A1 | 3/2013 | Figuly | |
| 2013/0131613 A1 | 5/2013 | Elkins | |
| 2013/0245578 A1 | 9/2013 | Bruder et al. | |
| 2013/0317459 A1 | 11/2013 | Bruder et al. | |
| 2013/0317460 A1 | 11/2013 | Bruder et al. | |
| 2014/0142667 A1 | 5/2014 | Biser | |
| 2014/0277303 A1 | 9/2014 | Biser et al. | |
| 2014/0288624 A1 | 9/2014 | Wasko | |
| 2014/0345543 A1 | 11/2014 | Saita | |
| 2015/0088236 A1 | 3/2015 | Bruder et al. | |

FOREIGN PATENT DOCUMENTS

| | | |
|---|---|---|
| EP | 0457977 | 2/1995 |
| EP | 0691113 A1 | 1/1996 |
| EP | 1652536 A1 | 5/2006 |
| EP | 1328225 | 3/2010 |
| FR | 2370479 | 6/1978 |
| GB | 1315431 A | 5/1973 |
| GB | 1417962 | 12/1975 |
| GB | 2228682 | 9/1990 |
| GB | 2259858 A | 3/1993 |
| JP | H07112021 A | 5/1995 |
| WO | 1992013576 | 8/1992 |
| WO | 0178797 A1 | 10/2001 |
| WO | 0222060 A1 | 3/2002 |
| WO | 2014143139 | 9/2014 |

OTHER PUBLICATIONS

International Search Report and Written Opinion for PCT/US2013/053221; dated Oct. 17, 2013; 10 pgs.
ZMedica—QuikClot Sport Silver; date unknown; 1 pg.
File History for U.S. Appl. No. 10/341,806.
File History for U.S. Appl. No. 13/291,059.
Healthcare Packaging; date unknown; 3 pages.
Non-Patent Literature cited by EPO in Examination of EP 0691113 May 31, 1995.
Patent Owner Amended Infringement Contentions for U.S. Pat. No. 8,420,882 filed Jun. 24, 2014.
U.S. Appl. No. 60/232,826, filed Sep. 15, 2000.
U.S. Appl. No. 60/349,335, filed Jan. 14, 2002.
International Preliminary Examination report for PCT/US01/28908 dated May 27, 2003.
International Search Report for PCT/US01/28908 dated Jan. 24, 2002.
Supplementary European Search Report for EP Application 01 97 3065 dated Aug. 1, 2006.
Mraz, S. 2011. "Technology helps heal chronic wounds," Machine Design, online, 5 pp., accessed Jun. 30, 2015. <http://machinedesign.com/medical/technology-helps-heal-chronic-wounds>.
"Products," Cerdak Corporation, online, accessed Jun. 30, 2015 <http://www.cerdak.co.za/Products/>.
Home page, Cerdak Corporation, online, accessed Jun. 30, 2015 <http://www.cerdak.co.za/Home/>.

* cited by examiner

WOUND AND THERAPY COMPRESS AND DRESSING

CROSS REFERENCE TO RELATED APPLICATIONS

This application is a Continuation-in-Part of: U.S. Non-Provisional patent application Ser. No. 13/956,727 filed Aug. 1, 2013, which is a Continuation of U.S. Non-Provisional patent application Ser. No. 10/380,803 filed on May 30, 2003, filed as application No. PCT/US2001/028908 on Sep. 17, 2001, which claims priority to U.S. Provisional Patent Application No. 60/232,826 filed on Sep. 15, 2000; U.S. Non-Provisional patent application Ser. No. 13/956,717 filed Aug. 1, 2013, which is a Continuation-in-part of U.S. Non-Provisional patent application Ser. No. 13/832,626 filed on Mar. 15, 2013, which is a Continuation-in-part of U.S. Non-Provisional patent application Ser. No. 13/291,059 filed on Nov. 7, 2011, which is a Continuation of U.S. Non-Provisional patent application Ser. No. 10/380,803 filed on May 30, 2003 filed as application No. PCT/US2001/028908 on Sep. 17, 2011, which claims priority to U.S. Provisional Patent Application No. 60/232,826; and U.S. Non-Provisional patent application Ser. No. 13/832,626 filed Mar. 15, 2013, which is a Continuation-in-part of U.S. Non-Provisional application Ser. No. 13/291,059 filed on Nov. 7, 2011, which is a Continuation of U.S. Non-Provisional application Ser. No. 10/380,803 filed on May 30, 2003 filed as application No. PCT/US2001/28908 on Sep. 17, 2001, all of which are hereby incorporated herein by reference.

FIELD OF THE INVENTION

The present invention relates in general to moist-heat therapy wound dressings and compresses. More particularly, the present invention relates to a wound dressing or compress optionally containing antimicrobial silver providing a germ and microbial free environment within the article.

BACKGROUND OF THE INVENTION

Modern wound dressings are designed to promote healing by providing a moist, warm or heated, wound environment. Warming a wound promotes healing by increasing blood flow to the area. Moisture in a wound is also very important to the healing process because it helps cells grow and divide, and reduces scarring. Available modern dressings may be dampened or moistened and then heated, for example, by microwave heating. Concurrent with the development of these dressings is the concern regarding a potential for microbial colonization of the wound. Antibiotics are available to combat infections but many people are allergic to certain antibiotics and antibiotic usage can cause gastrointestinal upset or other side effects. Further, excessive use of antibiotics has been blamed for the occurrence of treatment-resistant bacteria.

Blepharitis is a common and ongoing condition where the eyelids become inflamed (swollen), with oily particles and bacteria coating the eyelid margin near the base of the eyelashes. This annoying condition causes irritation, itchiness, redness, and stinging or burning of the eyes. While the underlying causes of blepharitis aren't completely understood, it can be associated with a bacterial eye infection, symptoms of dry eyes or certain types of skin conditions such as acne rosacea. Anterior blepharitis affects the outside of the eyelid where your eyelashes are attached. This can be caused by bacterial (or sometimes viral) infection. If left untreated, anterior blepharitis can lead to thickened and inward-turned or outward-turned eyelids and even vision problems from in-turned eyelashes damaging the cornea. Posterior blepharitis is a condition that results from a dysfunction of the eye's tiny oil glands (meibomian glands) in the eyelids at the base of the eyelashes. When meibomian glands become clogged from posterior blepharitis, it can also can cause a stye or chalazion to form. Posterior blepharitis also leads to thickened eyelid margins and crusty eyelids. With this type of blepharitis, tears can even look foamy.

Moist heat therapy applied by an area compress may also be beneficial to the treatment of arthritic or sprained joints, strained muscles, back pain, rheumatoid arthritis, or in any treatment where heat might be applied through or to the skin to promote circulation therein and thereunder. In such applications where no wound exudates contaminate therapy materials, reusability of the compress is an attractive cost-efficient design feature. Bacterial presence can cause dermatological problems to the treated area and further, a growing microbial colony in a reusable compress can cause the spread of infection through cross contamination when handled. This may represent a particular threat to therapy patients, many of whom have persistent or slow-healing injuries or compromised immunity systems.

A growing strategy for reducing the potential for infection or bacterial growth in a wound or on skin tissue under moist heat therapy is the incorporation of noble metal antimicrobials into the therapeutic wound dressing. The most prevalent such metal in use is silver due to its relative lack of cytotoxic effects and wide spectrum of antimicrobial effectiveness. Medical materials and instruments are available which provide the emission of silver metal or silver compounds to provide an antimicrobial effect. Such available dressings, once moistened, release silver into the surrounding liquid. The dressing thereby becomes an effective antimicrobial barrier. The silver, however, is consumed and lost in the process. Such products are inherently not conveniently reusable.

In both moist heat therapy wound dressings and compresses, bacterial and fungal growth can also cause unpleasant odor and unsightly discoloration which may adversely affect the morale of the patient. Thus there is a need in general for dressings and compresses designed to maintain sterility therein and to also provide microbial free moisture.

SUMMARY OF THE INVENTION

In example embodiments, the present invention provides a wound dressing and/or therapy compress having a granular fill material permanently loaded with at least one antimicrobial agent. The at least one antimicrobial agent comprises a form of silver, which form of silver may comprise atomic silver or a composition of silver. The dressing or compress thus comprises a fluid permeable shell and a backing, each of which is attached to the other to define a plurality of fill enclosures therebetween, and a fill material enclosed within the respective enclosures. A fluid permeable outer cover may be provided to protect the dressing or compress. The dressing may be used to shelter and protect a wound while absorbing exudate, and may also provide and maintain a heated and/or moist environment to promote the healing of the wound. The compress may be used to deliver moist heat therapy to an arthritic or sprained joint or strained muscle area.

In other aspects, example embodiments of the invention relate to a wound dressing and/or therapy compress having a granular fill material such as a hydrophilic zeolite or molecular sieve material, optionally loaded with at least one metallic antimicrobial agent, such as for example a silver, copper, copper oxide, gold, magnesium oxide, aluminum oxide, titanium dioxide, zinc oxide, cobalt, nickel, zirconium, molybdenum, tin, lead and/or other metals, metal oxides, metal ions, metal particles or nanoparticles, and alloys, mixtures or combinations thereof. The dressing or compress preferably comprises a flexible and body part conformable treatment device having a fluid-permeable shell and a backing, each of which is attached to the other to define at least one, and preferably a plurality of fill enclosures therein, and a particulate fill material enclosed and loosely contained within the respective enclosure(s). A fluid-permeable removable and replaceable outer cover may optionally be provided to protect the dressing or compress.

In a first example, the invention relates to an article for therapy and treatment of at least one eye. The article includes a backing for application to the at least one eye and at least one receiver positioned to align with the at least one eye. The article also includes at least one pod detachably secured within the at least one receiver. The at least one pod includes material for delivering therapy and treatment to the at least one eye.

In another example, the invention relates to an article for delivering moist heat therapy and treatment of at least one eye. The article includes a mask for application to the at least one eye. The mask includes at least one indented pocket positioned to align with the at least one eye. The article also includes at least one pod detachably secured within the at least one indented pocket. The at least one pod includes material for delivering moist heat therapy and treatment to the at least one eye.

In a still further example, the invention relates to an article for delivering moist heat therapy and treatment of at least one eye. The article includes a mask for application to the at least one eye. The mask includes at least one indented pocket positioned to align with the at least one eye. The article also includes at least one pod detachably secured within the at least one indented pocket. The at least one pod includes hydrophilic zeolite molecular sieve particles comprising at most twenty percent weight content of silver for delivering moist heat therapy and treatment to the at least one eye. The article also includes medicament dispensed toward the at least one eye by the at least one pod.

In a still further example, the invention relates to a method of treating an eye of a subject. The method includes removably attaching a pod to a receiver portion of a mask. The pod includes a moist heat delivery material. The method includes applying the mask to an eye area of the subject with the pod held proximal to the eye by the mask to deliver moist heat therapy to the eye.

The shell and backing are joined to form at least one, and preferably a plurality of enclosures there between. The enclosures may contain the loaded fill material. The presence of the antimicrobial agent within all or some of the fill material promotes a germ and microbial free environment at and near the lower shell and within the dressing or compress. The dressing or compress may be washable and reusable.

DETAILED DESCRIPTION OF THE INVENTION

Figure 1:
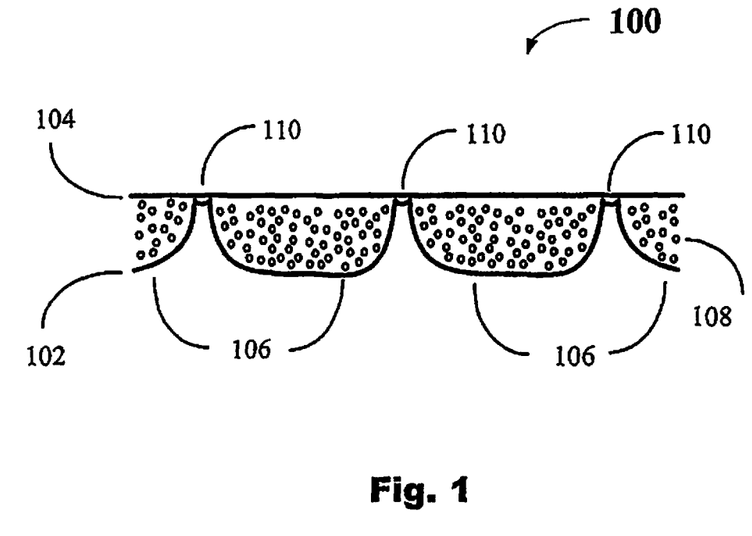
FIG. 1 is a partial side cross-sectional view of a dressing or compress according to an example embodiment of the present invention.

Referring now to FIGS. 1-4, and as best illustrated in FIG. 1, a dressing or compress 100 is illustrated having a lower shell 102 and a flexible upper backing 104 which are joined or otherwise fastened to one another to form a series of enclosures 106 there between. The enclosures are provided for the containment and relatively uniform distribution of a plurality of fill granules 108 placed therein. The enclosures may be fashioned as filled pods which are draped from the backing. The shell 102 forms the contact surface of the dressing or compress used to drape or form the bottom of the filled enclosures which are to be placed against the tissue to be treated, and to conform to the shape of the treatment area. The backing forms the smoother outer surface of the dressing or compress facing away from the treatment area.

Figure 2:
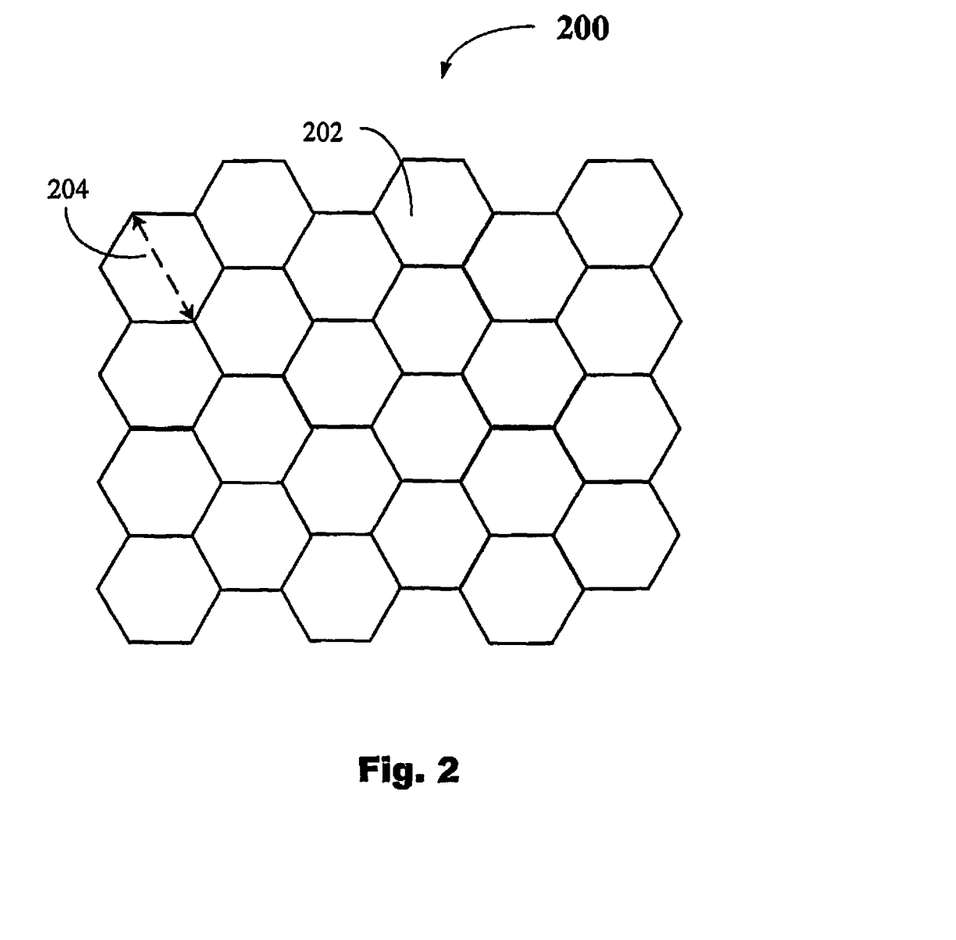
FIG. 2 is partial plan view of an exemplary hexagonal enclosure pattern according to an example embodiment of the present invention.

The enclosures 106 may be defined as hexagons using patterned seams 110 for local symmetry and efficient regular plane division. An illustrative hexagonal pattern 200 of enclosures 202 is illustrated in FIG. 2. The enclosures might also be fashioned as circles, octagons, or of any desired shape as may be appropriated for the desired treatment. The enclosures may be selectively sized as appropriate to the application. Each hexagonal shaped enclosure 202 has a lengthwise dimension 204 extending from a first corner to an opposite second corner thereof. For example, and not by way of limitation, this dimension may be in the range of from approximately one inch to approximately four inches in length. Large treatment areas such as the human torso or appendages may best be served with enclosures having a dimension 204 extending lengthwise for approximately 4 inches. Highly contoured areas such as the face may best be served with enclosures having a dimension 204 of approximately 1 inch in length.

Figure 3:
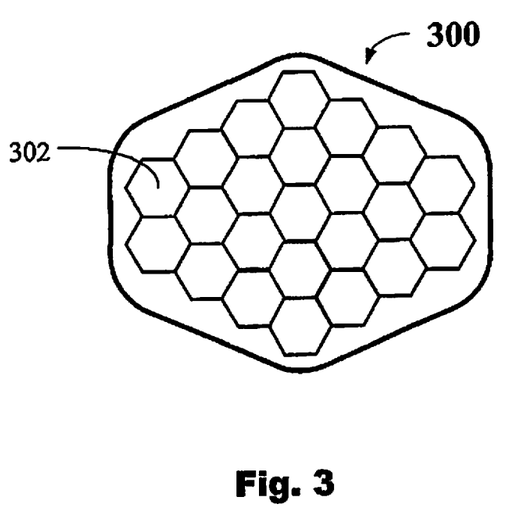
FIG. 3 is a plan view of an alternate exemplary dressing or compress with a hexagonal enclosure pattern.
Figure 4:
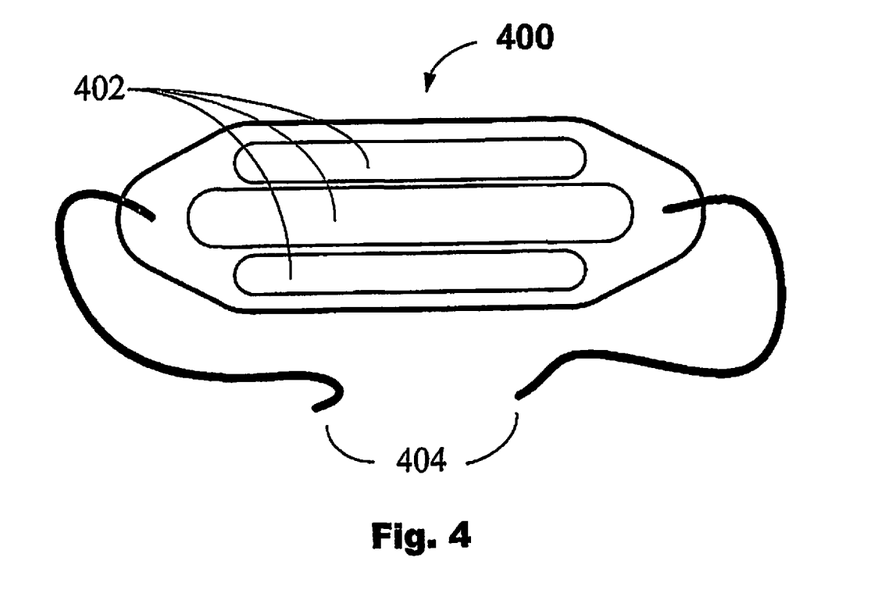
FIG. 4 is a plan view of a wrap compress with ties using the dressing or compress of the present invention.
Figure 5:
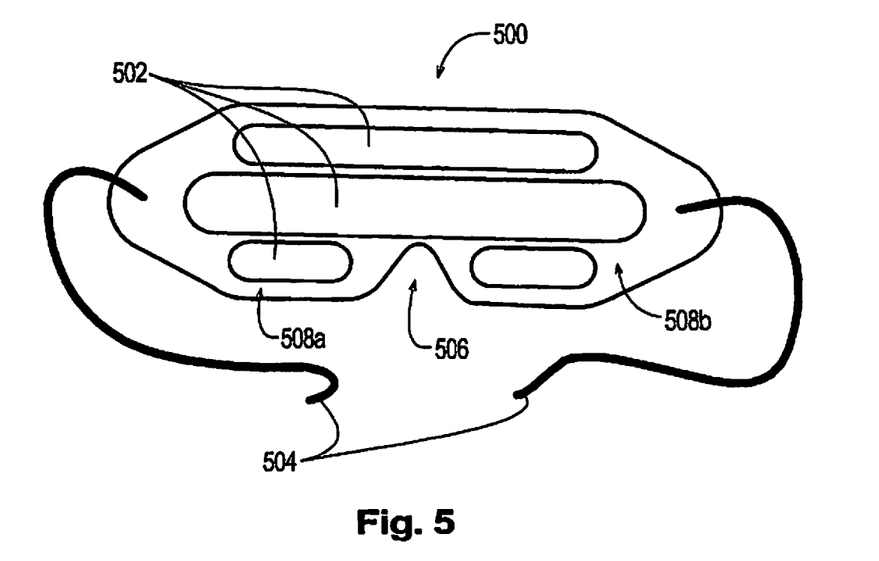
FIG. 5 is a plan view of a moist heat therapy compress in the form of an eye or nasal/sinus compress according to another example embodiment of the present invention.

An alternate dressing or compress 300 is illustrated in FIG. 3, having a plurality of hexagonal patterned enclosures 302. Each of the enclosures may also be formed as a channel-like rectangle, as illustrated in FIG. 4. The embodiment of the dressing or compress 400 is formed to have several channel enclosures 402 formed within a wrap compress having securing ties 404. So constructed, the dressing or compress 400 may be provided for the treatment of soreness or strains of the human back. In alternative applications, for example as illustrated in FIG. 5, the dressing or compress 500 is adapted for use as an eye compress for application of moist heat therapy to a subject's eyes with enclosures 502 for containing the fill granules and securing ties 504 for attachment around a patient's head, such as for treatment of dry-eye or other eye conditions; for moist heat therapy to a subject's sinus or nasal areas; and/or for treatment of other body parts of a human or animal subject or patient for wound care, epitheliazation, antibacterial, antimicrobial, antiviral, antifungal, anti-inflammatory, analgesic, moist heat therapy and/or other treatment purposes. In the eye compress configuration shown in FIG. 5, the flexible outer shell includes a generally triangular or trapezoidal nose cut-out area 506 at a medial portion of its lower edge, between first and second lobes 508*a*, 508*b* for covering areas over and around the user's left and right eyes when in use, with the ties or an elastic strap placed around the user's head, typically over the ears, to retain the compress 500 in place.

Figure 6:
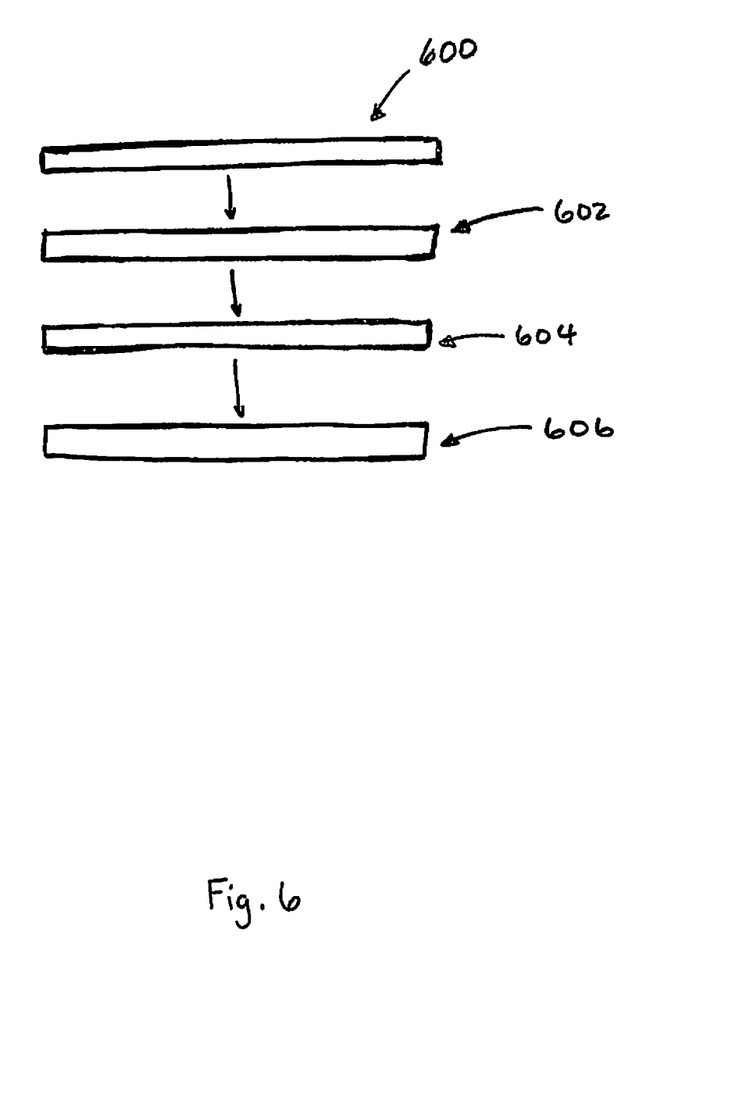
FIG. 6 is an exploded side view of a moist heat therapy compress of either FIG. 1 or FIG. 5 in use with an antibacterial wipe placed on an eye.

An alternative system is described in FIG. 6, whereby a heat compress 600 is combined with a heat transmissive pad or lid scrub or wipe 604 and is applied onto a skin surface 606, for example an eyelid. The pad or wipe 604 is preferably constructed of non-woven material and alternatively, material that can be RF or thermally sealed to hold an antibacterial medication. The example pad or wipe 604 can have a construction that is impregnated with antibacterial medication and can be effective in either a moist or dry condition. The antibacterial medication can include material, for example liposomes and/or microspheres. The pad or lid scrub or wipe 604 can be removably secured to the compress 600 for single use or multiple use. Alternatively, the antibacterial medication can be permanently incorporated into the compress 600, for example by permanently attaching the pad or lid scrub or wipe 604 to the compress or impregnating the medication into the compress directly, for single use or multiple use.

The example pad or wipe 604 is constructed to be moist-heat transmissive so that an application of moist-heat activates the release of the impregnated antibacterial medication onto the skin surface 606. The example pad or wipe 604 is constructed to prevent the impregnated antibacterial medication from passing back into the compress 600 during application. A one-way-valve or sheet barrier 602, disposable or semi-disposable, can be placed between the pad or wipe 604 and the compress 600 to prevent any antibacterial medication from the wipe from entering the compress. This one-way-valve 602 can be secured to the compress 600 with hook-and-loop or equivalent means.

The example pad or wipe 604 can have a round or oval disk shape with appropriate size and shape to be placed over a single eyelid. The disk 604 can be constructed of non-woven material. In use, two disks can be used, one over each eye. A plurality of the disk 604 can be stored within a jar containing antibacterial medication fluid, so as to pre-moisten the wipes during storage. In use, a pair of disks 604 are removed from the jar and one is placed over each eye of a user while the user is lying down. An appropriately-sized rectangular or mask-shaped layer of the non-woven one-way-valve barrier 602 is then placed over the disks 604 set on the eyes. The compress 600 can then be placed over the one-way-valve 602 for the desired treatment duration. Once treatment is completed, each disk 604 can be used to wipe the eyelid on which it was placed.

Alternatively, the disk 604 can be stored in a dry state with an integrated one-way-valve layer 602 covering one side. Once removed from packaging, the dry disk wipe 602 is applied with an appropriate volume of antibacterial treatment fluid on a side opposite the one-way-valve layer 602 and then used in a similar manner as described previously.

Alternatively, the disks 604 can be packaged in a single-use pair or can be cut out from a pore-gradient fabric before use.

The compress 600 can, for example, have a construction similar to the compress 100 in FIG. 1, or the compress 500 in FIG. 5 or an alternative design. In use with compress designs 100, 500, the pad or wipe 604 can secure to the compress through hook-and-loop or sewing for multiple use. Alternatively still, the pad or wipe 604 can be constructed as an independent single-use sheet and is discarded after application. The compress 600 can alternatively be constructed as an independent sheet for multiple uses.

During use on a skin surface 606 affected with a condition, for example blepharitis in an eyelid, the application of moist heat from the compress 600 will expand the pores on the skin surface. When the pores are expanded, the transdermal passage and effectiveness of the antibacterial medication from the pad or wipe 604 through the skin is increased.

The size of the enclosures and overall dressing are selected to serve the desired treatment. Selected single sites for treatment such as the eye may best be treated using a single enclosure dressing or compress appropriately sized and shaped to rest comfortably in the eye hollow of the human face. The dressing or compress may be shaped as a regular or irregular polygon, any smooth closed curve, or any closed combination of line segments and smooth curves. The invention is not limited to constructions conforming to or only serving the human body. The invention provides a potentially useful treatment for the ailments of mammals and any animals benefiting from the healing properties of moisture and/or heat therapy.

A fluid-permeable, i.e., a vapor-permeable and/or a liquid-permeable protective outer cover (not illustrated) may be provided to encompass the compress. This may be preferable to limit contamination of the dressing or compress. For the treatment of open wounds, an uncovered disposable dressing (not illustrated) may be preferred for optimal formable contact with, and healing of, the exposed tissues.

The fill contained within the enclosure or enclosures may comprise a synthetic porous crystalline granular aluminosilicate zeolite, commonly used as a molecular sieve material, or other substances with similar properties. The fill material may further comprise other inert additives and physical matrices without affecting the antimicrobial and hydrous efficacies of the fill. Silver loading of the fill may be attained by the process of ion-exchange, as known. In this process, a solution containing atomic silver or a composition of silver bathes, or is passed through, a bed of the fill granules 108 (FIG. 1). An ion-exchange column method, as known in the art, may be performed in which an aqueous solution containing atomic silver or a composition of silver may be passed through a column bed of the fill granules, and the eluted solution may again be passed through the bed or may receive additional silver and then be again passed through the bed.

Various ion-exchange schedules known in the art may optionally be applied to produce retention of the silver. The final content by weight of the atomic silver or silver composition may be as high as twenty percent of the final loaded fill granules. The loaded fill granules produced by ion-exchange will exhibit high retention of the silver even under subsequent exposure to fluids and microwave irradiation. The fill granules may comprise a blend of both loaded and unloaded zeolite or optionally a substance retaining silver. The presence of the atomic silver or silver composition will not interfere with the useful properties of the fill granules such as the moisture desorption and adsorption properties which may be desirable in the use of the dressing or compress. The inherent hydrophilic nature of the zeolite provides that a substantial water content is available therein by absorption from the atmosphere. The water so absorbed may be sufficient, or may be supplemented by manually added water, for providing the microwave responsive water content of the dressing or compress. The compositions of silver used may include but are not limited to, silver compounds, and silver salts such as silver chloride and silver nitrate.

The optional presence of the silver within the fill granules contained in the enclosure of the invention, if provided, provides anti-microbial properties to the dressing or compress. The ion-exchange loaded fill granules will retain the silver despite microwave heating as may be required in the use of the dressing or compress, which prevents the release of silver into a treated wound if the invention is used as a dressing. Further, the retention of the silver within the fill granules provides assured antimicrobial performance in a reusable and potentially washable, if so desired, moist heat therapy compress. Optionally, the wound dressing and/or therapy compress comprises a granular fill material such as a hydrophilic zeolite or molecular sieve material, with at least one metallic antimicrobial agent, such as for example a copper, copper oxide, gold, magnesium oxide, aluminum oxide, titanium dioxide, zinc oxide, cobalt, nickel, zirconium, molybdenum, tin, lead and/or other metals, metal oxides, metal ions, metal particles or nanoparticles, and alloys, mixtures or combinations thereof deposited therein.

The compress or dressing of the present invention(s) alternatively comprises fill granules such as a hydrophilic zeolite with or without anti-microbial metal(s) disposed therein. Example anti-microbial metal(s) include adsorbent technologies employing beads of activated alumina, silica gel, bentonite and molecular sieves, with or without metals. For wound dressing applications, the provision of anti-microbial metal(s) may be preferable. For therapeutic compress applications, the provision of anti-microbial metal(s) is optional. Moist heat therapy applied by an area compress may be beneficial to the treatment of arthritic or sprained joints, strained muscles, back pain, rheumatoid arthritis, or in any treatment where heat might be applied through or to the skin of a human or animal patient or subject, to promote circulation therein and there under. In such applications where no wound exudates contaminate (imbedded metals may not be incorporated into the molecular sieve granules when used for this purpose), reusability and ability to wash the compress are attractive cost-efficient design features. Thus, example embodiments of the invention comprise a washable and/or reusable compress.

In the described embodiments of the invention, the lower shell and the upper backing are each constructed of materials known in the art. Each may therefore be comprised of multilayered laminates, for example, with pore sizes selectable to meet the moisture transmission and retention properties desired for the specific treatment sought. The dressing or compress is adapted to be placed and to remain in intimate contact with the area to be treated to maintain a heated and/or moist environment thereabout. Dressing or compress constructions using woven textiles of natural fibers have been found to have limited spatial conformance to the various shapes, dimples, wrinkles and joints offered by the human body, although these materials may be used if so desired.

Accordingly, preferred dressing or compress constructions will use formable woven and non-woven synthetic materials or combinations thereof which may include, but are not limited to, synthetic olefin, polyester, urethane, and nylon. The shell and the backing may be fastened together across the area of the dressing or compress with a fill material, the fill granules 108, received there between. The shell and the backing may be fastened to one another by methods which may include, but are not limited to, adhesive attachment, RF welding, ultra-sonic attachment, sewing, or patterned heat application using a template or forming die to form a seal. To provide for the secure placement of the dressing or compress, peripheral or attachment fastening devices may be included which may comprise the desired number of Velcro®-type fasteners, adhesives, high tactility polymer materials, and/or material ties.

Throughout the construction of the dressing or compress, attention and care is taken in the selection of materials regarding thermal response to microwave heating. For design simplicity, all synthetic, microwave non-responsive materials may be selected to provide that the fill and/or water content of a moistened dressing or compress provide the only substantial thermal response to microwave irradiation.

Figure 7:
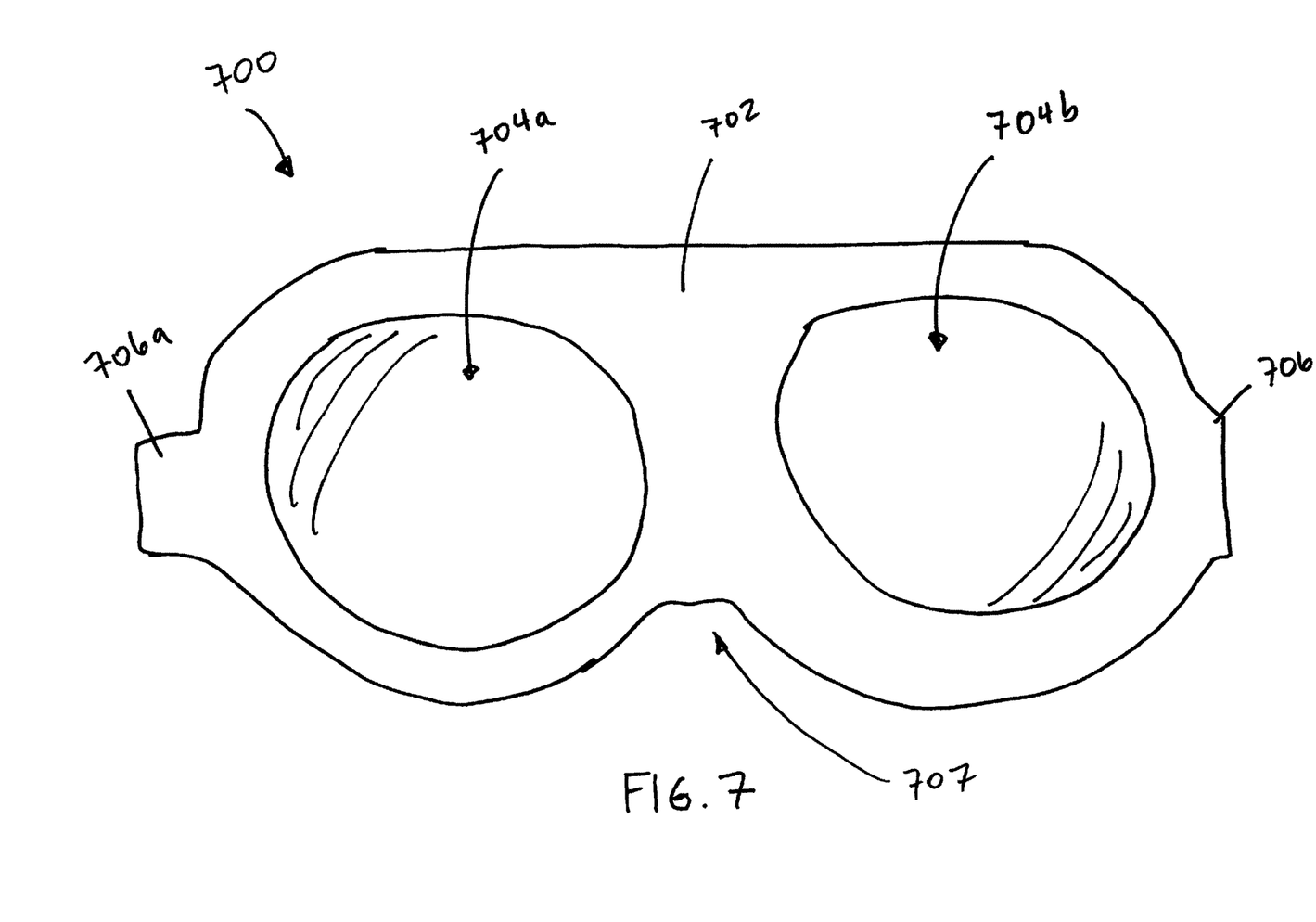
FIG. 7 is a plan view of a mask with indents for receiving removable moist heat therapy pods, according to another example embodiment of the present invention.
Figure 8:
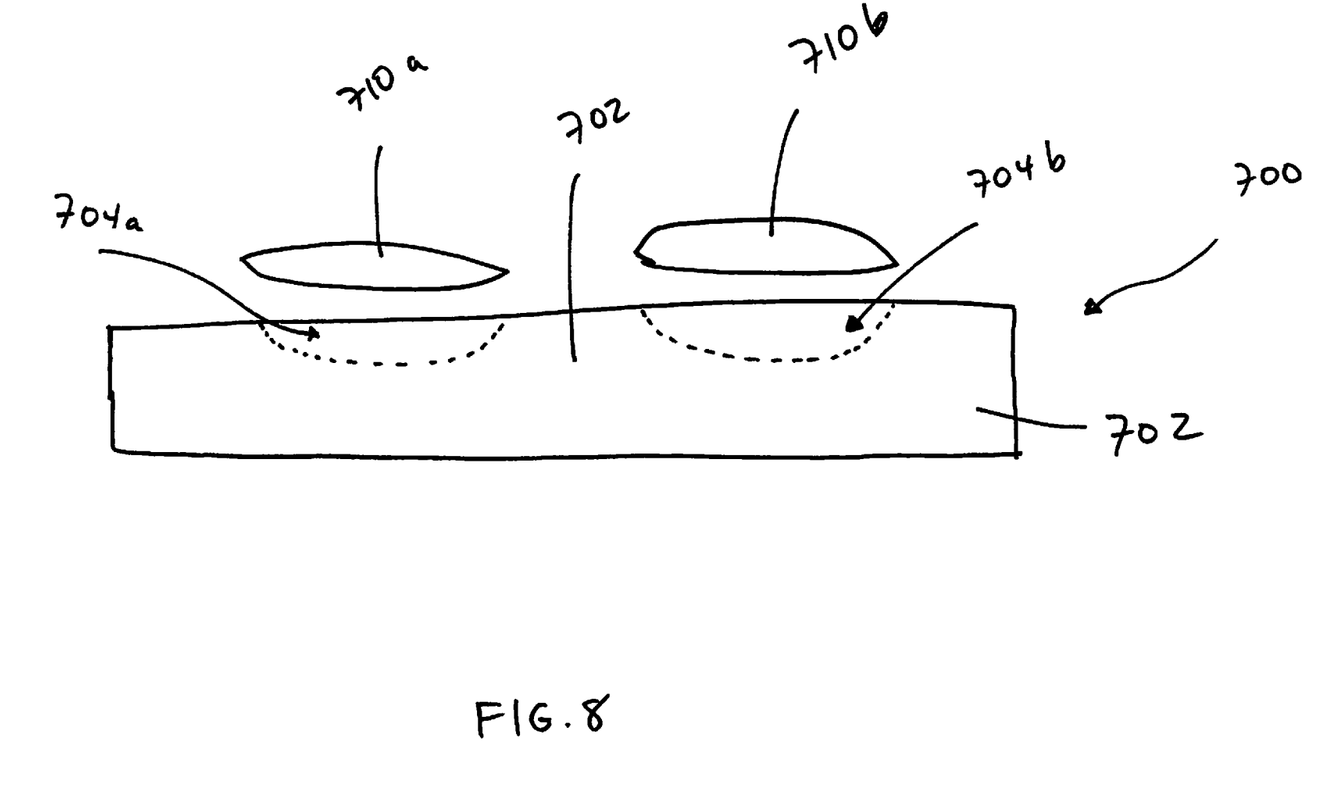
FIG. 8 is an exploded side view of the mask of FIG. 7 and example moist heat therapy pods.
Figure 9:
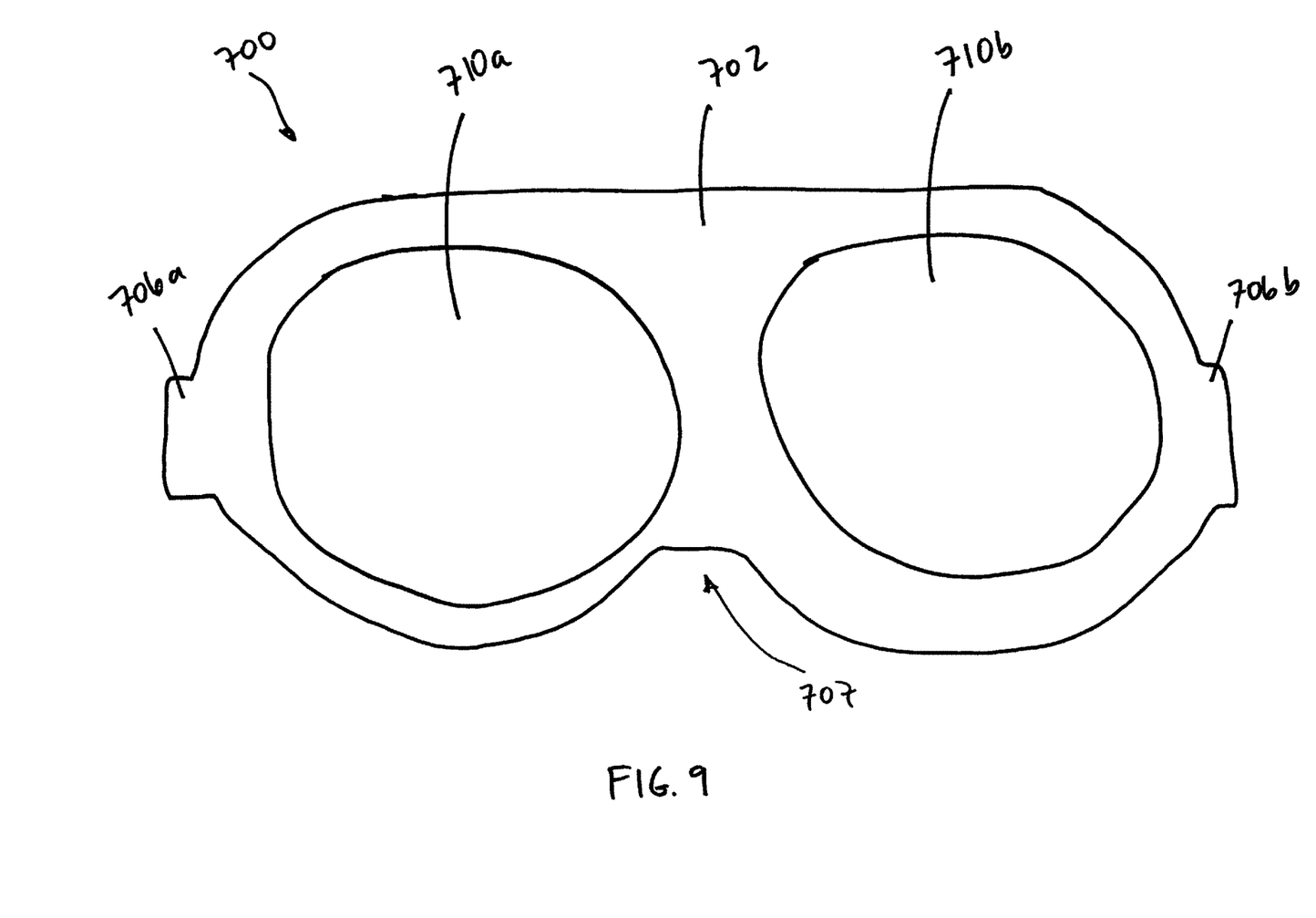
FIG. 9 is a plan view of the moist heat therapy pods secured to the mask, both of FIG. 8.

Another example embodiment includes a mask or compress that is designed to accommodate separate pods, one for each eye. The pods are preferably capable of delivering moist heat therapy, cold therapy and treatment to treat conditions on the eyelids, for example meobian gland-dysfunction and blepharitis with moist heat and puffiness or inflammation with cold therapy. As depicted in FIGS. 7-9, a mask or compress 700 can include a main support body 702 formed of foam, polyester or other materials, with a single head support strap or dual supports 706a, 706b to fit on the ears. The mask main body 702 also includes a notch 707 for receiving a user's nose.

The mask 700 is intended to be worn over the eyes, and has a pair of receivers 704a, 704b positioned on the main body 702 to sit over each eye when the mask is worn. Preferably, the receivers 704a, 704b are permanently-formed indents or pockets in the mask 700. More preferably, these indents or pockets 704a, 704b are positioned on the side of the mask 700 that directly faces the eyes of the user when worn. The mask 700, including the body 702, receivers 704a, 704b and supports 706a, 706b can have a monolithic uniform construction of soft and flexible material, for example foam or polyester.

In use, a pair of removable pods 710a, 710b are received within the receivers 704a, 704b. Preferably, the pods 710a, 710b are detachably secured within the receivers 704a, 704b through the use of an attachment mechanism, for example hook-and-loop fastener material secured to both the pods and the receivers. This removability allows the pods 710a, 710b to be disposable after use, or cleaned and re-used. The pods 710a, 710b can have a soft construction that is able to contain formulations or materials capable of delivering therapy treatment, for example moist heat and cold treatments. Example formulations or materials include hydrophilic zeolite granules and optionally silver, other materials as described above, or cold pads.

Additionally, as depicted and described specifically with respect to FIG. 6 above, medicaments can be applied and used with respect to the pods 710a, 710b. For example, antibiotics can be infused or injected into the formulation in the pods 710a, 710b. Alternatively, discs similar to those in FIG. 6 can be set in the receiver pockets 704a, 704b and then covered with the pods 710a, 710b, or alternatively the medication discs are attached to the back face of the pods, for example by hook-and-loop fasteners, and applied between the pod and the eye. These discs can be injected with medicament or antibiotics or manually applied to the discs, for example with a spray. The medicament can be in dry or wet form. Similarly to the embodiment in FIG. 6, when the pods 710b, 710b are heated, the medicament is released towards the eyelids. Following use, the pods 710a, 710b, and if applicable the discs, can be removed from the receivers 704a, 704b to be discarded or cleaned.

Although several embodiments of the invention have been disclosed in the foregoing specification, it is understood by those skilled in the art that many modifications and other embodiments of the invention will come to mind to which the invention pertains, having the benefit of the teaching presented in the foregoing description and associated drawings. It is thus understood that the invention is not limited to the specific embodiments disclosed hereinabove, and that many modifications and other embodiments are intended to be included within the scope of the invention. Moreover, although specific terms are employed herein, they are used only in a generic and descriptive sense, and not for the purposes of limiting the described invention. The words "a," "an," or "the" can mean one or more, depending upon the context in which the words are used hereinabove.

What is claimed is:

1. An article for therapy and treatment of at least one eye, the article comprising:
    a backing for application to the at least one eye, the backing comprising at least one receiver positioned to align with the at least one eye; and
    at least one pod configured for detachable securement within the at least one receiver, the at least one pod comprising material for delivering therapy and treatment to the at least one eye;
    wherein the material for delivering therapy and treatment comprises granules loosely contained within the at least one pod, wherein the granules consist essentially of hydrophilic zeolite.

2. The article of claim 1, wherein the granules comprise at most twenty percent weight content of silver.

3. The article of claim 1, wherein the at least one receiver comprises a pocket indented from the backing.

4. The article of claim 1, wherein the at least one pod is detachably secured within the at least one receiver with hook-and-loop fastener material.

5. The article of claim 1, wherein the at least one pod delivers moist heat to the at least one eye.

6. The article of claim 1, wherein the at least one pod delivers cold therapy to the at least one eye.

7. The article of claim 1, further comprising medicament dispensed toward the at least one eye by the at least one pod.

8. The article of claim 7, wherein the medicament is impregnated into the at least one pod.

9. The article of claim 7, further comprising at least one disc comprising the medicament, the at least one disc detachably secured between the at least one eye and the at least one pod.

10. An article for delivering moist heat therapy and treatment of at least one eye, the article comprising:
    a mask for application to the at least one eye, the mask comprising at least one indented pocket positioned to align with the at least one eye; and
    at least one pod configured for detachable securement within the at least one indented pocket, the at least one pod comprising material for delivering moist heat therapy and treatment from the material to the at least one eye;
    wherein the material for delivering therapy and treatment comprises hydrophilic zeolite molecular sieve granules loosely contained within the at least one pod.

11. The article of claim 10, wherein the hydrophilic zeolite molecular sieve granules comprise at most twenty percent weight content of silver.

12. The article of claim 10, further comprising medicament dispensed toward the at least one eye by the at least one pod.

13. The article of claim 12, wherein the medicament is impregnated into the at least on pod.

14. The article of claim 12, further comprising at least one disc comprising the medicament, the at least one disc detachably secured between the at least one eye and the at least one pod.

15. An article for delivering moist heat therapy and treatment of at least one eye, the article comprising:
    a mask for application to the at least one eye, the mask comprising at least one indented pocket positioned to align with the at least one eye;
    at least one pod detachably secured within the at least one indented pocket, the at least one pod comprising a moist heat delivery material, the moist heat delivery material comprising granules loosely contained within the at least one pod, the granules consisting essentially of hydrophilic zeolite molecular sieve particles comprising at most twenty percent weight content of silver for delivering moist heat therapy and treatment to the at least one eye; and
    medicament dispensed toward the at least one eye by the at least one pod.

16. The article of claim 15, wherein the hydrophilic zeolite molecular sieve particles are configured to allow repeated absorption and dissipation of moisture to and from the hydrophilic zeolite material.

17. The article of claim 15, wherein the medicament is impregnated into the at least on pod.

18. The article of claim 15, further comprising at least one disc comprising the medicament, the at least one disc detachably secured between the at least one receiver and the at least one pod.

19. A method of treating an eye of a subject, said method comprising removably attaching a pod to a receiver portion of a mask, the pod comprising a moist heat delivery material, the moist heat delivery material comprising granules loosely contained within the pod, the granules comprising hydrophilic zeolite molecular sieve particles, and applying the mask to an eye area of the subject with the pod held proximal to the eye by the mask to deliver moist heat therapy to the eye.

20. The method of claim 19, further comprising application of a medication material to the pod and delivery of said medication material with the moist heat therapy to the eye.

* * * * *